(12) United States Patent
Weischedel

(10) Patent No.: US 6,265,870 B1
(45) Date of Patent: Jul. 24, 2001

(54) EDDY CURRENT SENSOR ASSEMBLY FOR DETECTING STRUCTURAL FAULTS IN MAGNETICALLY PERMEABLE OBJECTS

(75) Inventor: Herbert R. Weischedel, South Windsor, CT (US)

(73) Assignee: NDT Technologies, Inc., South Windsor, CT (US)

(*) Notice: Subject to any disclaimer, the term of this patent is extended or adjusted under 35 U.S.C. 154(b) by 0 days.

(21) Appl. No.: 09/389,309

(22) Filed: Sep. 2, 1999

(51) Int. Cl.$^7$ .......................... G01N 27/82; G01N 27/90
(52) U.S. Cl. .................... 324/240; 324/220; 324/232; 324/242
(58) Field of Search .................... 324/219–221, 324/227, 232, 235, 240–243, 262

(56) References Cited

U.S. PATENT DOCUMENTS

| | | |
|---|---|---|
| 3,593,122 | * 7/1971 | Barton et al. .................... 324/220 |
| 3,845,381 | 10/1974 | Hart . |
| 4,105,972 | * 8/1978 | Smith .................... 324/220 |
| 4,310,796 | * 1/1982 | Braithwaite et al. .................... 324/220 |
| 4,495,465 | 1/1985 | Tomaiuolo et al. . |
| 4,659,991 | 4/1987 | Weischedel . |
| 4,827,215 | 5/1989 | van der Walt . |
| 4,855,676 | 8/1989 | Cecco et al. . |
| 5,036,277 | 7/1991 | van der Walt . |
| 5,128,613 | 7/1992 | Takahashi . |
| 5,198,765 | 3/1993 | van der Walt . |
| 5,237,270 | 8/1993 | Cecco et al. . |
| 5,293,117 | 3/1994 | Hwang . |
| 5,414,353 | 5/1995 | Weischedel . |
| 5,446,382 | 8/1995 | Flora . |
| 5,461,313 | * 10/1995 | Bohon et al. .................... 324/227 X |
| 5,751,144 | 5/1998 | Weischedel . |
| 5,864,237 | * 1/1999 | Laursen .................... 324/220 |
| 6,023,986 | 2/2000 | Smith et al. . |
| 6,037,767 | * 3/2000 | Crescenzo et al. .................... 324/220 |

FOREIGN PATENT DOCUMENTS 2 086 051   5/1982 (GB) .
58-22951    2/1983 (JP) .
8-285818    11/1996 (JP) .

OTHER PUBLICATIONS

German article, *Die Elektromagnetische Prufung von Drahtseilen* (The Electromagnetic Testing of Wire Cable) by Urs B. Meyer, Mitteilungen Aus Dem Institut Fur Elektrische Maschinen An Der Eth, 1973 Switzerland, pp. 107–109.

Thesis, *Ein Beitrag Zur Magnetinduktiven Querschnittsmessung Von Drahtseilen* (A Contribution to the Magnetic–Inductive Measurement of Wire Cable Cross–Sections) by Wolfgang Rieger, University of Stuttgart, 1983 Germany, pp. 49 and 98.

*Nondestructive Testing Handbook*, "Electromagnetic Testing Eddy Current, Flux Leakage and Microwave Nondestructive Testing" vol. 4, 1986 USA, pp. 212–215.

* cited by examiner

*Primary Examiner*—Gerard R. Strecker
(74) *Attorney, Agent, or Firm*—McCormick, Paulding & Huber LLP

(57) ABSTRACT

An eddy current sensor assembly of a magnetic inspection device is for nondestructive detection of structural faults in an elongated magnetically permeable object, such as a pipe. The sensor assembly has an auxiliary magnet including first and second auxiliary magnetic poles oppositely polarized relative to each other and spaced from one another for positioning and movement longitudinally relative to an elongated magnetically permeable object to be tested. The auxiliary magnet is to be interposed between primary magnets of the magnetic inspection device. A ferromagnetic member couples the first and second auxiliary magnetic poles. Compliant pole pieces such as magnetically permeable brushes are coupled to the auxiliary poles and are to be interposed between the auxiliary poles and the object to be inspected. An eddy current sensor is disposed between the auxiliary magnetic poles and includes a sensor body and a means coupled to the ferromagnetic member for urging the sensor body against an opposing surface of the magnetically permeable object to be inspected.

20 Claims, 8 Drawing Sheets

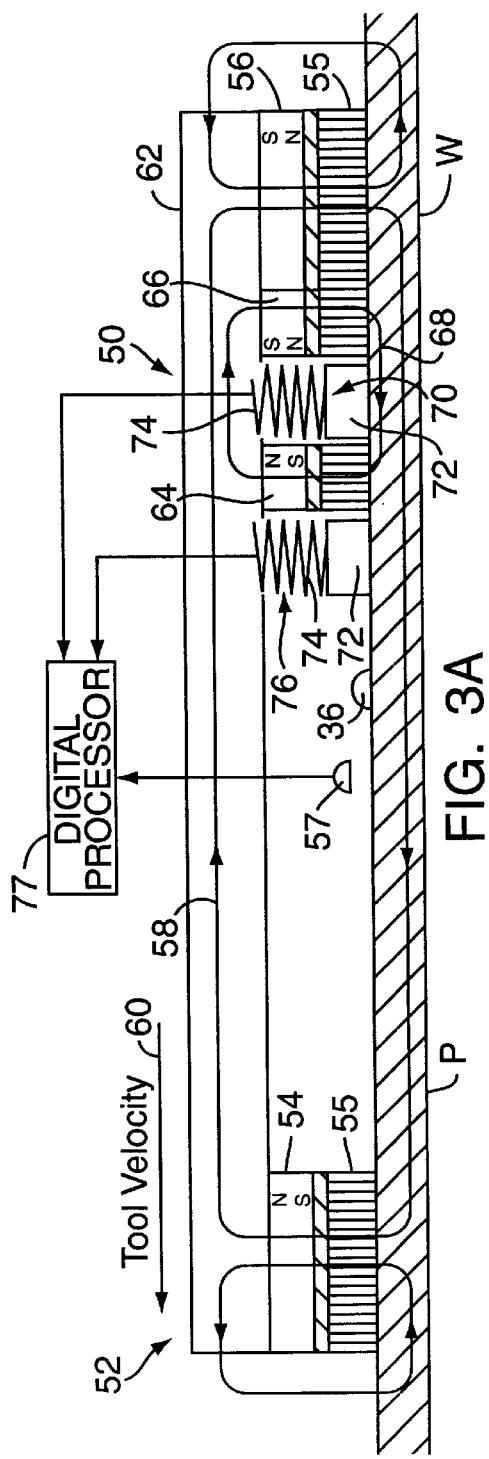
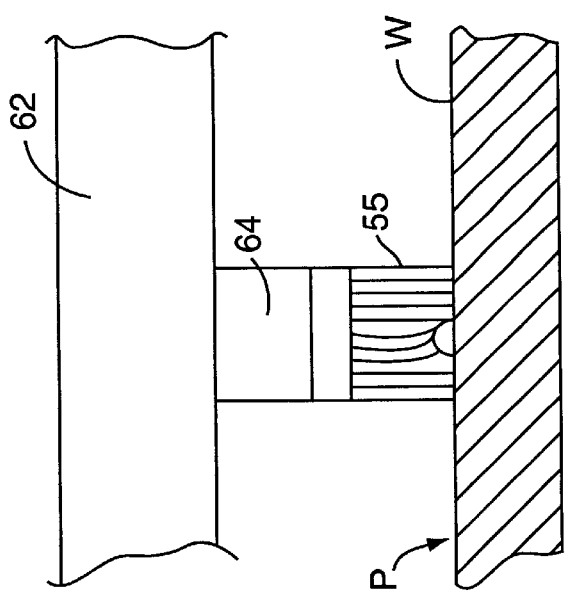

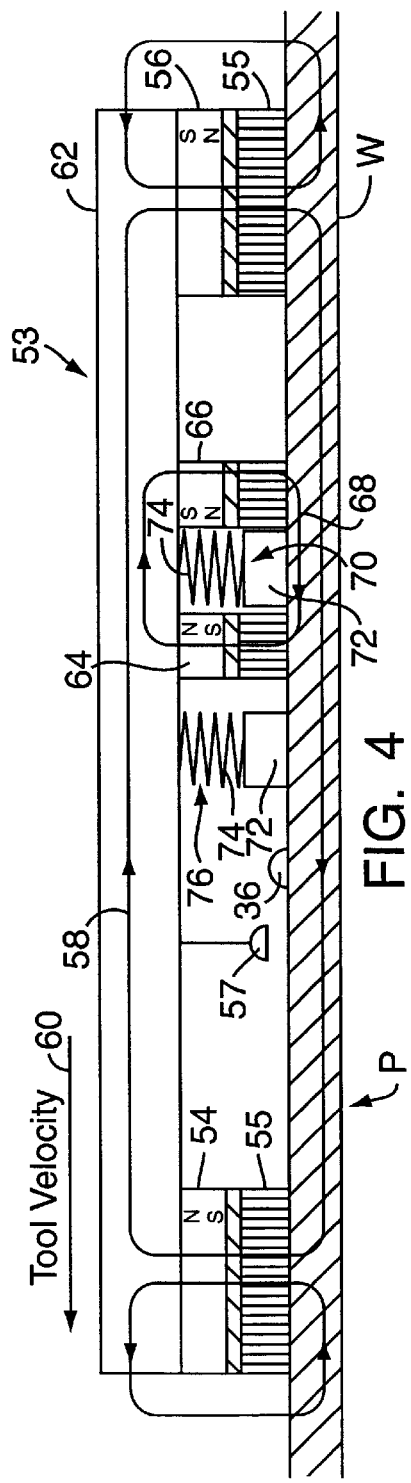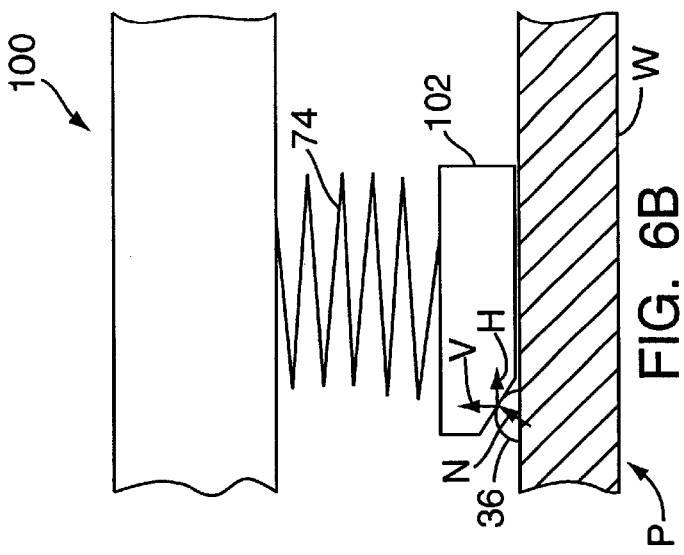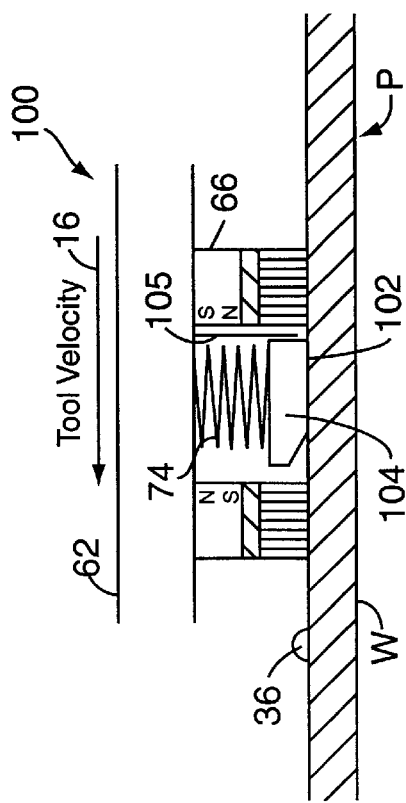
FIG. 4
FIG. 6A
FIG. 6B

EDDY CURRENT SENSOR ASSEMBLY FOR DETECTING STRUCTURAL FAULTS IN MAGNETICALLY PERMEABLE OBJECTS

BACKGROUND OF THE INVENTION

The present invention generally relates to a sensor for nondestructive inspection of magnetically permeable objects such as wire cables, rods, pipes and the like. The invention is concerned more particularly with an eddy current sensor assembly for detecting structural faults in the objects.

Eddy current (EC) devices are known for inspecting elongated magnetically permeable objects such as wire cables, rods, pipes, and the like for structural defects such as stress-corrosion cracks. One such device shown in my U.S. Pat. No. 5,751,144, the disclosure of which is herein incorporated by reference, includes magnet means which induces a magnetic flux which magnetically saturates the object along a longitudinal section. The magnet means and the induced magnetic flux move progressively and longitudinally relative to the object whereby a longitudinal section of the object experiences a changing magnetic flux which induces eddy currents. An eddy current change detecting means is provided on the magnet means and is to be positioned adjacent to the relatively moving object to detect changes in eddy currents which are representative of structural faults in the object.

Eddy current inspection and sensing methods for faults in objects made of ferromagnetic materials suffer from two critical problems. First, the high permeability of the ferromagnetic material acts as a shield because of the frequency-permeability-conductivity term that appears in skin depth calculations. Thus, full-wave penetration of the object wall is difficult to achieve. Second, the permeability, coercive force and remanence of steel are influenced by material properties, by internal stresses and by structural conditions. These magnetic influences depend on the selection of the initial materials and the melting, foundry, rolling and annealing processes. Because these magnetic characteristics are not well controlled during manufacture and handling, magnetic properties can vary in a random fashion along the length of the elongated object. Localized permeability variations, in the absence of auxiliary magnetization, usually lead to noise levels that prevent sufficiently high sensitivities during testing.

There are three ways to increase the through-wall penetration depth and the signal-to-noise ratio of EC inspections. First, the object can be magnetically saturated to decrease its magnetic permeability and, thereby, increase skin depth. Magnetic saturation also decreases localized permeability variations, which in turn decreases distortions of the inspection signals, thereby improving the signal-to-noise ratios. Second, the skin depth can be increased by lowering the excitation frequency. And, third, the strength of the excitation signal can be increased.

For through-wall inspections, it is therefore necessary to magnetically saturate the material to be inspected by a DC magnetic field. When ferromagnetic material is magnetically saturated, its relative permeability approaches a value of one (i.e., that of air). When thus saturated, the material behaves like a non-ferromagnetic material and permeability variations will not affect the EC inspection. The low relative permeability decreases the background noise and improves the signal-to-noise ratio so that discontinuity signals can be sensed. In addition to noise reduction, the DC magnetization method decreases the skin effect which is otherwise problematic when applying an alternating magnetic field associated with conventional eddy current methods.

Feasibility experiments have shown that a simple DC magnetic saturation method is easily implemented. However, for a reliable through-wall detection of structural faults such as axial slits, two necessary conditions must be simultaneously satisfied. First, the magnetically permeable elongated object must be magnetically saturated or nearly saturated. Second, significant eddy currents must be induced so that eddy current changes representative of structural faults can be readily detected. The previous two conditions will hereinafter be referred to as the "necessary conditions".

Unfortunately, the necessary conditions are somewhat incompatible with each other because the magnet means moving relative to the tested object induces a changing magnetic field which, according to Lenz's law, excites eddy currents together with an associated magnetic field that opposes the change in the magnetic field which produced these eddy currents. Therefore, the induction of eddy currents retards the diffusion of the magnetic flux through the object wall so as to oppose magnetic saturation of the pipe. These motion induced eddy currents will be called Self-Excited Eddy Currents (SEECs) hereafter. Full magnetic saturation (or near saturation) is achieved only after the eddy currents (the SEECs) have decayed toward zero magnitude. In other words, for a simple implementation of an SEEC method, the independent control of the magnetic saturation together with the simultaneous induction of strong SEECs is not possible. As such, prior SEEC apparatus and methods suffer from the difficulty of simultaneously achieving the necessary conditions for reliable structural fault detection.

A solution for improving the reliability of structural fault detection is to provide a magnetic inspection device having two primary and opposite poles which induce a magnetic flux to place the object at least near magnetic saturation. At least one auxiliary pole is positioned on the inspection device between the primary poles and serves to boost the level of the magnetic flux induced by the primary poles so as to strengthen induced eddy currents during relative movement of the inspection device and the object. At least one sensor positioned on the inspection device detects eddy current changes which are representative of structural faults. A drawback with current auxiliary pole methods for inducing eddy currents is that the eddy current sensors and auxiliary poles are lifted off of the pipe wall when the magnetic inspection device contacts a bead of a girth weld or longitudinal weld connecting adjacent pipe sections. The lifting of the eddy current sensor and auxiliary poles cause a distortion in the readings of the eddy current sensor which can cause a structural fault to be undetected if a structural fault is located near or at a girth weld.

Accordingly, it is a general object of the present invention to provide an eddy current sensor assembly that eliminates or otherwise minimizes distortion in detecting changes in eddy currents when a magnetic inspection device contacts a girth weld or other projection or obstruction in an inspected pipe wall.

SUMMARY OF THE INVENTION

One aspect of the present invention resides in an eddy current sensor assembly of a magnetic inspection device for nondestructive detection of structural faults in an elongated magnetically permeable object. The sensor assembly has magnet means including first and second magnetic poles oppositely polarized relative to each other and spaced from one another for positioning and movement longitudinally relative to an elongated magnetically permeable object to be tested. A ferromagnetic member couples the first and second magnetic poles. Compliant pole pieces such as magnetically permeable brushes are coupled to the poles to be interposed between the poles and the object to be inspected. An eddy current sensor is disposed between the first and second magnetic poles and includes a sensor body and a means coupled to the ferromagnetic member for urging the sensor body against an opposing surface of the magnetically permeable object to be inspected.

Another aspect of the present invention resides in a magnetic inspection device for nondestructively detecting structural faults in magnetically permeable elongated objects. The inspection device includes first and second primary magnetic poles oppositely polarized relative to each other and spaced from one another for positioning and movement longitudinally relative to an elongated magnetically permeable object to be tested. The first primary magnetic pole is positioned upstream of the second primary magnetic pole relative to magnetic pole movement. A ferromagnetic member magnetically couples the first and second primary magnetic poles. First and second auxiliary magnetic poles are magnetically coupled to the ferromagnetic member and interposed between the first and second primary magnetic poles. The first auxiliary magnetic pole is positioned upstream of the second primary magnetic pole. The first and second auxiliary magnetic poles respectively have the same poling as the first and second primary magnetic poles. The primary magnetic poles induce a static magnetic flux through a longitudinal section of an object extending between the primary magnetic poles to at least a near-saturation level. The auxiliary magnetic poles boost the magnitude of the induced static magnetic flux in a portion of the object adjacent to the auxiliary magnetic poles. The primary magnetic poles and the auxiliary magnetic poles induce circumaxial eddy currents and associated opposing magnetic fluxes in moving portions of the object adjacent to the first primary magnetic pole and the first auxiliary magnetic pole. Compliant pole pieces are coupled to the primary and auxiliary magnetic poles and are to be interposed between the poles and the object to be inspected. An eddy current sensor is disposed between the first and second auxiliary magnetic poles. The sensor includes a sensor body and a means coupled to the ferromagnetic member for urging the sensor body against an opposing surface of the magnetically permeable object to be inspected.

An advantage of the present invention is that when the eddy current sensor assembly contacts a weld bead or other projection in the inspected object the distance between the magnetic poles of the sensor assembly and the object is substantially maintained to prevent distortion of the eddy current signal generated by the sensor assembly.

Another advantage of the present invention is that the sensor body of the eddy current sensor is biased toward the object to be inspected in order to maintain continuous contact with the object as the sensor body moves over a weld bead or other projection for further preventing distortion of the eddy current signal.

BRIEF DESCRIPTION OF THE DRAWINGS

FIG. 3A schematically illustrates an eddy current sensor assembly embodying the present invention employed in a magnetic inspection device.

FIG. 3B schematically illustrates the eddy current sensor assembly of FIG. 3A as its magnetic pole moves over a weld bead.

FIG. 4 schematically illustrates an eddy current sensor assembly in accordance with another embodiment of the present invention.

FIG. 6A schematically illustrates an eddy current sensor assembly including a coiled spring and chamfered sensor body in accordance with the present invention.

FIG. 6B schematically illustrates the chamfered sensor body of FIG. 6A as it contacts a weld bead.

DESCRIPTION OF THE PREFERRED EMBODIMENTS

Figure 1A:
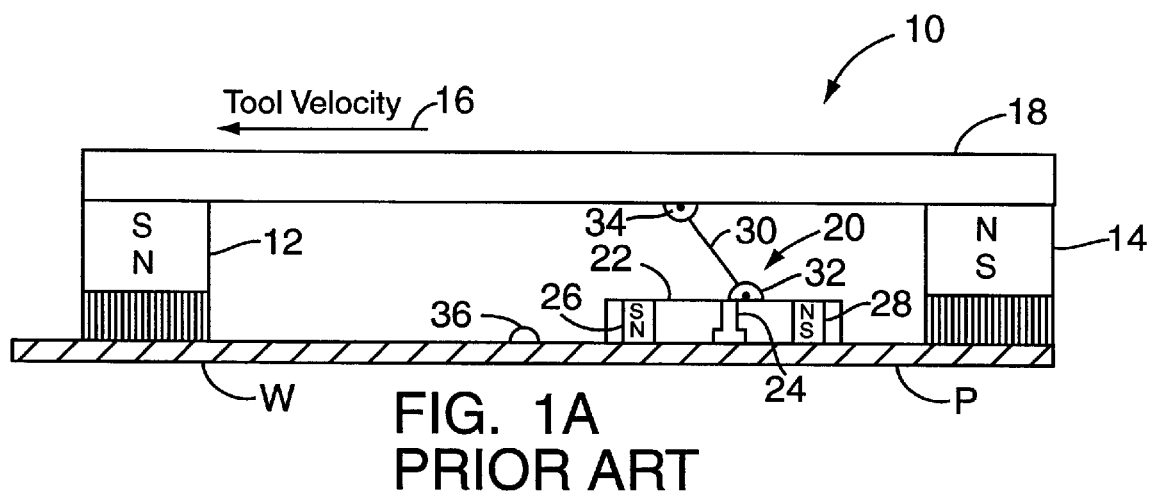
FIG. 1A schematically illustrates a known magnetic inspection device including an eddy current sensor assembly.
Figure 1B:
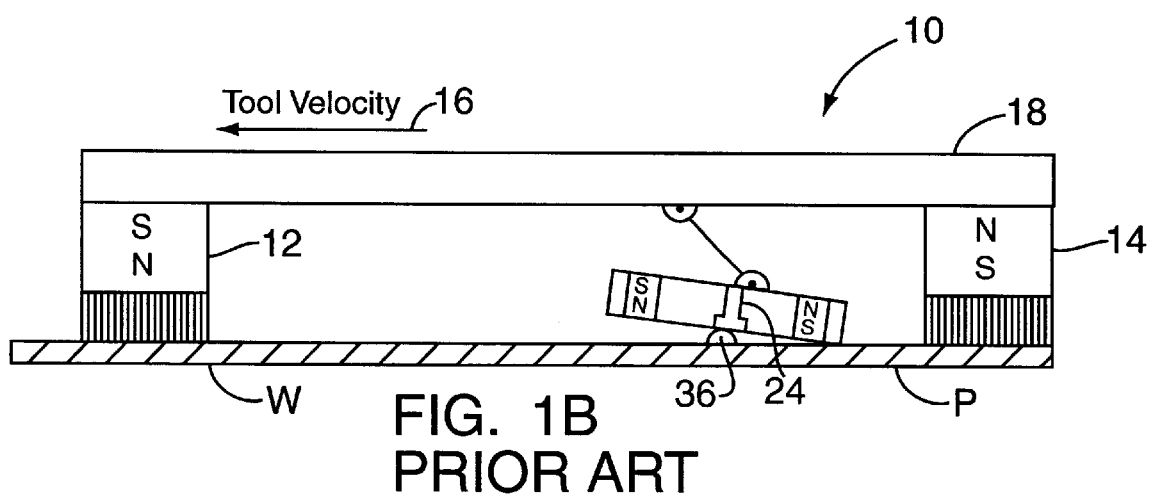
FIG. 1B schematically illustrates the eddy current sensor assembly of FIG. 1A as it moves over a weld bead.

With reference to FIGS. 1A and 1B, a known magnetic inspection device for nondestructively inspecting a magnetically permeable elongated object such as a pipe P for structural faults is schematically illustrated and generally designated by the reference number 10. For clarity, only the bottom portion of the device 10 is shown and only the bottom longitudinal section of the pipe wall W is illustrated as being inspected by the device. Preferably, the inspection device 10 extends substantially circumaxially about the object and may be located either internally of the object (as shown) or externally of the object.

The inspection device 10 includes a permanent magnet having first and second primary poles 12 and 14 for inducing a primary magnetic flux in a pipe wall W of the pipe P. Each of the primary poles 12 and 14 is oppositely poled relative to one another and is radially polarized relative to the pipe P. The inspection device as shown in FIGS. 1A and 1B moves leftwardly relative to the pipe P as indicated by the arrow 16 whereby the first primary pole 12 leads the second primary pole 14 relative to inspection device movement. The primary poles 12 and 14 are magnetically coupled by a primary ferromagnetic member such as a ferromagnetic bar 18 which completes a magnetic flux circuit having a forward portion through a longitudinal section of the pipe P extending between the primary poles 12 and 14, and a return portion through the bar 18.

The inspection device 10 further includes a flux-changing means embodied as an auxiliary magnet assembly 20 for inducing substantial eddy currents, whereby eddy current changes representative of structural faults can be readily detected. The auxiliary magnet assembly 20 is located between the first and second primary poles 12, 14, and includes a housing 22 for supporting an auxiliary magnet and an eddy current sensor 24. The auxiliary magnet has first and second auxiliary poles 26 and 28 for inducing the substantial eddy currents in a portion of the pipe wall W between the auxiliary poles. The eddy current sensor 24 is located between the first and second auxiliary poles 26 and 28. The housing 22 is adjustably coupled to the ferromagnetic bar 18 of the inspection device 10 by means of a link member 30 having first and second longitudinal ends which are respectively pivotally coupled to the housing 22 and the bar 18 by means of hinge members 32, 34. As the inspection device 10 contacts a projection 36 such as a weld bead from a girth weld or longitudinal weld in the pipe wall W, the housing 22, along with the eddy current sensor 24 supported therein and the auxiliary poles 26, 28, will be moved by the weld bead or other projection or obstruction radially away from the pipe wall W (see FIG. 1B). As the auxiliary poles 26, 28, the eddy current sensor 24 and any magnetic flux leakage sensors are moved off of the pipe wall W, the magnetic flux pattern will become distorted which, in turn, causes a massive distortion of self excited eddy current and magnetic leakage flux signals respectively detected by eddy current and magnetic flux leakage sensors. This makes structural fault inspection in the vicinity of welds impossible. Since structural faults such as stress-corrosion cracking and weld seam corrosion frequently occur close to and inside girth and longitudinal welds, structural fault inspection capability near these welds is highly desirable.

Figure 2:
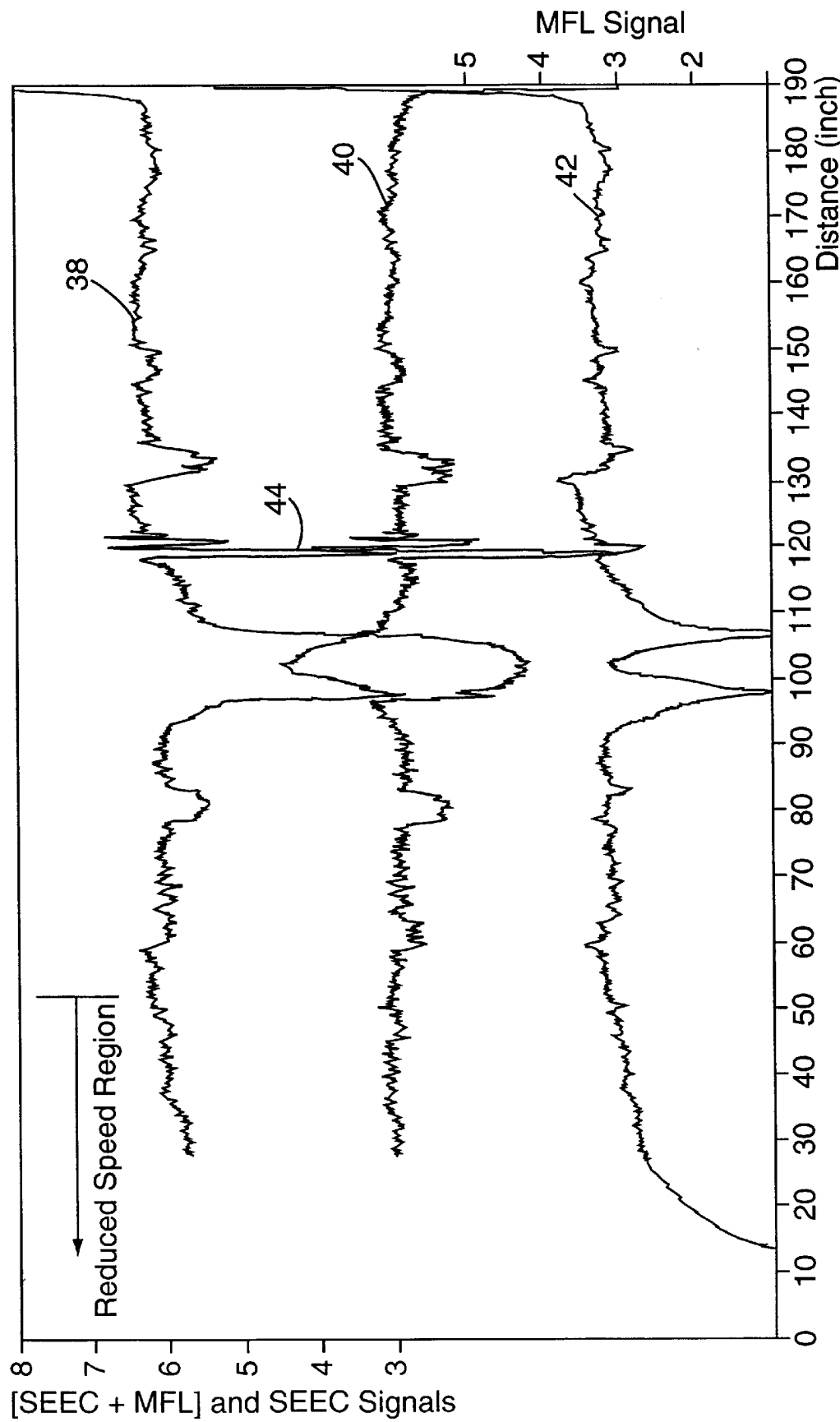
FIG. 2 graphically illustrates various signals detected by the magnetic inspection device of FIG. 1.

FIG. 2 illustrates signal distortion received by such a conventional inspection device near a girth weld. Signal 40 is the difference of signals detected by an eddy current sensor and magnetic flux leakage sensor (not shown in FIG. 1); signal 38 is the eddy current signal, and signal 42 is the magnetic flux leakage signal. All three signals 38, 40, 42 show an abrupt distortion at 44 corresponding to where the sensors are being moved away from a pipe wall W as the sensor housing contacts a girth weld.

Turning now to FIGS. 3A and 3B, an eddy current sensor assembly in accordance with a preferred embodiment of the present invention is generally designated by the reference number 50. The sensor assembly 50 is part of a magnetic inspection device 52 for nondestructively detecting structural faults in an elongated magnetically permeable object, such as a pipe wall W.

The magnetic inspection device 52 includes a permanent magnet having first and second primary poles 54 and 56 for inducing a primary magnetic flux 58 in the pipe wall W. Each of the primary poles 54 and 56 is oppositely poled relative to one another and is radially polarized relative to the pipe P. A magnetic flux leakage sensor 57 may be located between the primary poles 54 and 56 for detecting magnetic leakage flux caused by variations in metallic cross-sectional area of the pipe wall W. The inspection device 52 as shown in FIG. 3 moves leftwardly relative to the pipe P as indicated by the arrow 60 whereby the first primary pole 54 leads the second primary pole 56 relative to inspection device movement. The primary poles 54 and 56 are magnetically coupled by a primary ferromagnetic member such as a ferromagnetic bar 62 which completes a magnetic flux circuit having a forward portion through a longitudinal section of the pipe P extending between the primary poles 54 and 56, and a return portion through the bar 62.

The primary poles 54, 56 are magnetically coupled to the pipe wall W by means of compliant pole pieces such as magnetically permeable brushes 55, preferably steel brushes, attached to the primary poles 54, 56 and extending radially therefrom to the pipe wall W. The magnetic force of attraction pulls the primary poles 54, 56 toward the inside of the pipe wall. The brushes 55 couple the magnetic flux from the magnetic poles into the pipe wall. Brushes provide less variation in magnetic coupling than steel blocks or plates, leading to more consistent flux levels in the pipe. The lack of brushes with the auxiliary poles 26 and 28 of the auxiliary magnet assembly 20 of FIG. 1 causes the distortion shown in FIG. 2. This means that, as the auxiliary poles move across the bead of a girth weld 36, its magnetic poles are lifted off of the pipe wall causing a distortion of the magnetic flux. The brushes 55 not only couple the magnetic field into the pipe, but they also act as an integral part of the mechanical dynamics of the magnetization system. The brushes 55 absorb the shock that can result at internal penetrations such as weld roots, restrictions, and dents in the pipe wall. For magnetic inspection devices with solid magnetic shoes, the dynamic performance is not as smooth, but the magnetic coupling is better. Spring mounting systems (not shown) may be used to attach the magnets to the body of the magnetic inspection device. These systems help center the device in the pipe, and they absorb and damp vibrations.

The eddy current sensor assembly 50 is an auxiliary magnet assembly for inducing substantial eddy currents, whereby eddy current changes representative of structural faults can be readily detected. The auxiliary magnet assembly 50 is located between the first and second primary poles 54, 56. The eddy current sensor assembly includes an auxiliary magnet having first and second auxiliary poles 64 and 66 for inducing the substantial eddy currents in a portion of the pipe wall W between the auxiliary poles. Preferably, as shown in FIGS. 3A and 3B, the auxiliary poles 64, 66 are closer to the second primary pole 56 which lags the first primary pole 54 relative to inspection device movement, and the second auxiliary pole is adjacent to or is part of the second primary pole 56. The second primary pole 56 and the second auxiliary pole 66 may be structurally distinct from one another or may form a single pole serving both the primary and auxiliary magnetization of the object to be inspected. If the primary and auxiliary poles are a single pole, the size of such pole should be the total size of the primary and auxiliary poles that would be employed separately from each other. As shown in FIGS. 3A and 3B, the first auxiliary pole 64 is magnetically oriented in the same direction as the first primary pole 54, and the second auxiliary pole 66 is magnetically oriented in the same direction as the second primary pole 56, whereby the auxiliary poles 64, 66 induce an auxiliary magnetic flux 68 which reinforces the primary magnetic flux. The reinforcement of the primary magnetic flux results in substantial eddy currents so that any changes to the eddy currents which are representative of structural faults are more readily detectable. The auxiliary poles 64, 66 are magnetically coupled to the pipe wall W by means of magnetically permeable brushes 55 attached to the auxiliary poles 64, 66 and extending radially therefrom to the pipe wall W.

The eddy current sensor assembly 50 further includes an eddy current sensor 70 located between the first and second auxiliary poles 64 and 66. The eddy current sensor 70 includes a sensor body 72 and a means 74 for attaching the sensor body 72 to the ferromagnetic bar 62 and for urging the sensor body 72 radially toward and into contact with an opposing portion of the pipe wall W. The eddy current sensor assembly 50 may also include an additional eddy current sensor 76, including a sensor body 72 and urging means 74. As shown in FIG. 3A, the urging means 74 is a resilient member such as a coil spring in compression, but may take other practical forms as will be discussed with reference to the following figures.

The additional eddy current sensor 76 is particularly useful in situations where it is likely that the eddy current sensors will also detect a signal component due to other types of faults such as loss of cross-sectional area or other localized faults. The two signals generated by the eddy current sensors 70 and 76 may then be solved as two simultaneous equations having two variables to determine the component due to structural faults. A digital processor 77, such as a computer, communicates with the sensors 57, 70 and 76 for determining the location and magnitude of structural faults along the object to be tested in response to signals generated by the sensors when detecting changes in eddy currents.

In operation, as the magnetic inspection device 52 moves leftwardly as shown in the direction of the arrow 60, the sensor body 72 of the additional eddy current sensor 76 contacts a bead of a girth weld or projection 36 which moves the sensor body away from the pipe wall W in the radial direction, thereby further compressing the resilient means 74. The compressed resilient means 74 continues to urge the sensor body 72 of the additional sensor 76 against the girth weld as the sensor body moves thereover so that the sensor body is maintained in constant contact with the pipe wall W. The constant contact with the pipe wall W of the sensor body 72 of the additional eddy current sensor 76 as it moves past the girth weld 36 permits the eddy current sensor 76 with accuracy to detect changes in eddy currents due to structural faults occurring at or near the girth weld in the pipe wall W.

As the inspection device 52 continues to move leftwardly, the girth weld bead 36 contacts the brushes 55 of the first auxiliary magnetic pole 64. As shown in FIG. 3B, the brushes 55 absorb the shock caused by such contact in order to minimize any movement of the eddy current sensor assembly 50 such as the auxiliary magnetic poles 64, 66 relative to the pipe wall W. Minimizing relative movement between the auxiliary magnetic poles 64, 66 and the pipe wall W substantially maintains the level of the magnetic flux induced in the pipe wall, and consequently prevents distortion in the detection of eddy current changes by the eddy current sensors 70 and 76. The inspection device 52 further moves leftwardly such that the eddy current sensor assembly 50 is in continuous contact with the girth weld 36 as it contacts the eddy current sensor 70 and the second auxiliary magnetic pole 66 in a way similar to the previously described contact with the sensor 76 and the first auxiliary pole 64.

FIG. 4 schematically illustrates an eddy current sensor assembly 53 in accordance with a further embodiment of the present invention. For simplicity of illustration, the digital processor for processing the sensor signals is not shown in this and the following embodiments. With respect to further embodiments, like elements with previous embodiments are labelled with like reference numbers. The sensor assembly 53 is similar to the sensor assembly 50 of FIGS. 3A and 3B except for the location of the sensor assembly relative to the primary poles 54 and 56 of the inspection device. As shown in FIG. 4, the eddy current sensor assembly 53 is disposed further from the second primary pole 56 and closer to the first primary pole 54 in comparison with the position of the eddy current sensor assembly 50 of FIGS. 3A and 3B. The location of the eddy current sensor assembly 53 further upstream of the second primary pole 56 relative to the location in FIGS. 3A and 3B may not be as accurate as the location in FIGS. 3A and 3B because the eddy currents generated by the first primary pole 54 may not have fully decayed toward zero preventing the pipe wall W from complete magnetic saturation.

Figure 5:
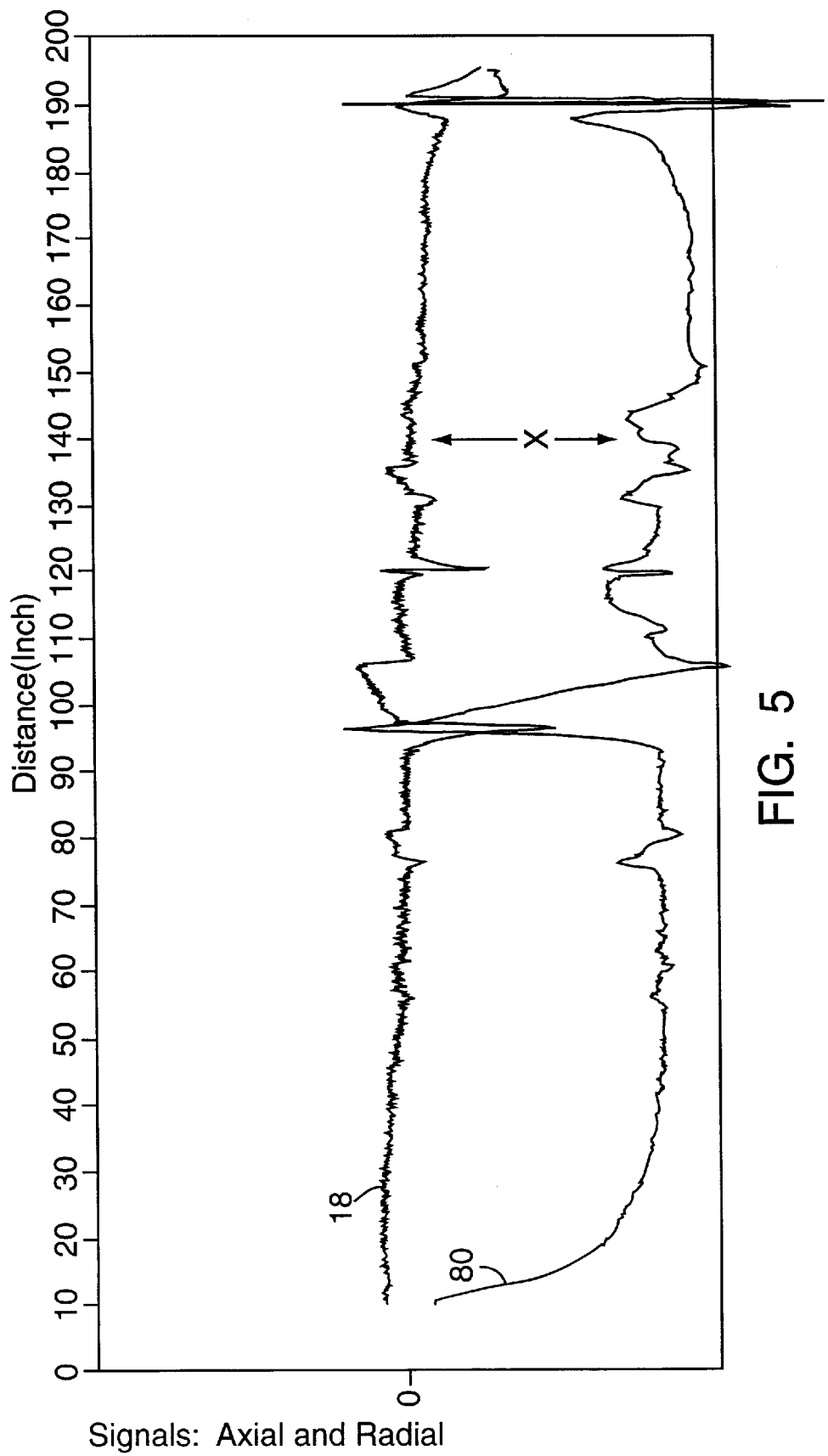
FIG. 5 graphically illustrates various signals detected by a magnetic inspection device of FIGS. 3A and 3B.

FIG. 5 illustrates the same pipe section as was inspected in FIG. 2, with the eddy current sensor assembly 50 of FIGS. 3A and 3B. Signal 78 indicates the axial component and signal 80 indicates the radial component of the magnetic field that is caused by SEECs. In contrast to FIG. 2, the signals 78 and 80 of FIG. 5 do not show the distortion near the weld bead (corresponding to the ordinate distance of 120 inches) that is otherwise caused by magnet lift-off described with respect to FIGS. 1 and 2.

FIGS. 6A and 6B schematically illustrates an eddy current sensor assembly 100 in accordance with another embodiment of the present invention. Ideally, an eddy current sensor moving in the axial direction of the pipe P should easily move in the radial direction if forced away from the pipe wall W by a girth weld or other obstruction. The eddy current sensor assembly 100 is similar to the assembly 50 shown in FIG. 3, except for the shape of a sensor body 102. The sensor body 102, coupled to the ferromagnetic bar 62 by means of the coil spring 74, defines a chamfer 104 at a leading edge to oppose a pipe wall W of a pipe P to be inspected. As shown in FIG. 6B, as the sensor body 102 moves leftwardly relative to the pipe P as shown by the arrow 16, the weld bead 36 or other projection asserts a force (shown by the arrow N) against the sensor body at the chamfer 104. The chamfer 104 facilitates the translation of the force N into horizontal and vertical components (shown by the arrow H and the arrow V respectively) for movement of the sensor body primarily in the radial direction in order to move the sensor body easily over the weld bead. A projection or stop 105 extending downwardly from the ferromagnetic bar 62 and interposed between the sensor body 102 and the second auxiliary pole 66 prevents the sensor body 102 from contacting and damaging the second auxiliary pole as it partly moves in a horizontal direction upon contacting a weld bead 36. The sensor body 102 urged against the pipe wall W by the coil spring 74 maintains continuous contact with the pipe wall as it travels over the weld bead 36 to prevent distortion of the eddy current changes detected by the sensor body.

Figure 7:
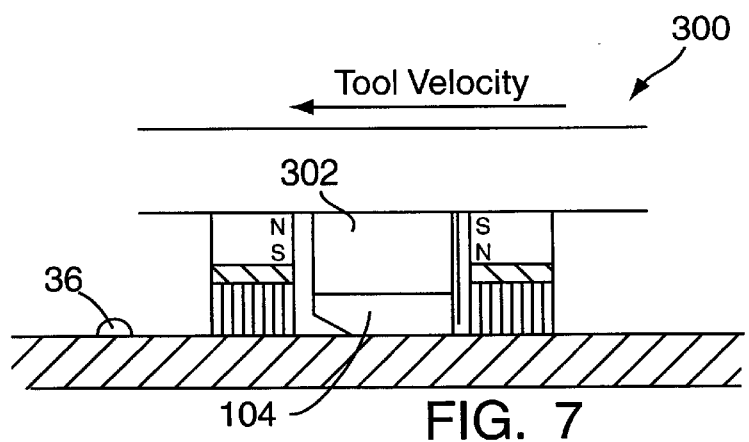
FIG. 7 schematically illustrates an eddy current sensor assembly including a elastic block and chamfered sensor body in accordance with the present invention.

FIG. 7 schematically illustrates an eddy current sensor assembly 300 in accordance with a further embodiment of the present invention. The eddy current sensor assembly 300 is similar to the eddy current sensor assemblies of FIGS. 5 and 6, except that the resilient member is in the form of an elastic or compression block 302, preferably made of rubber. Advantages of employing the rubber block 302 for the resilient member is its low cost, simple construction and durability.

Figure 8A:
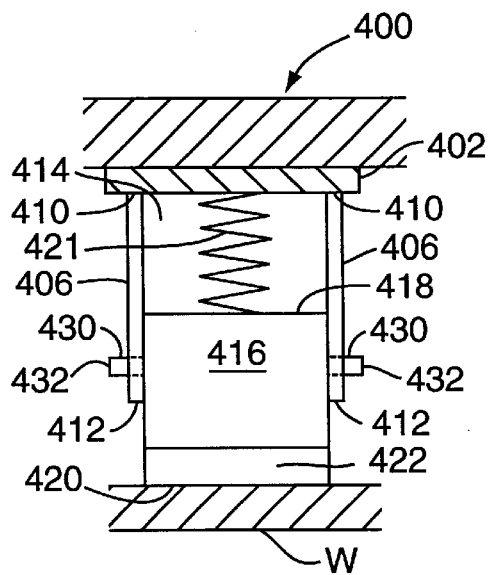
FIG. 8A is a schematic, side elevational view of an eddy current sensor assembly including guide plates and angled coil springs in accordance with the present invention.
Figure 8B:
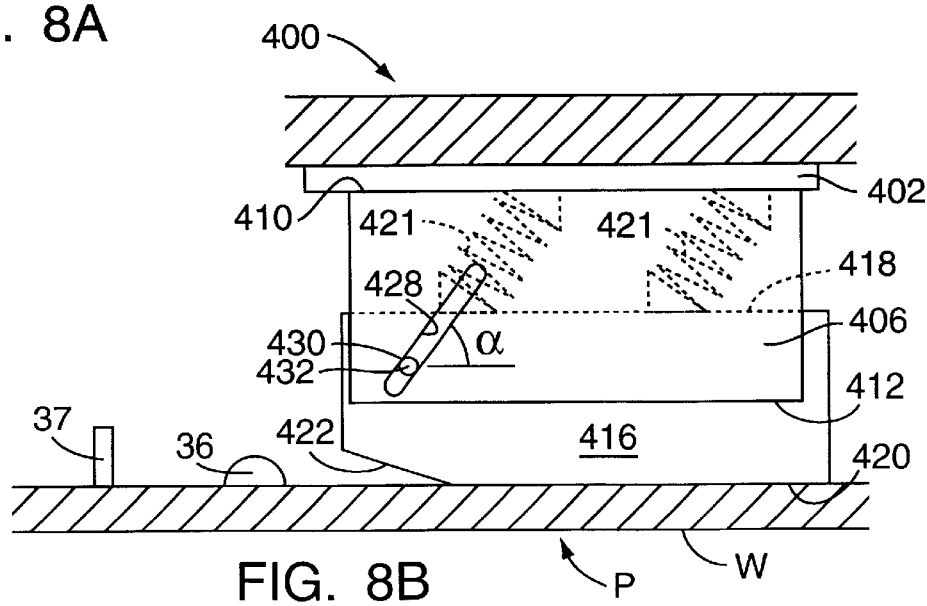
FIG. 8B is a schematic, front elevational view of the eddy current sensor assembly of FIG. 8A.

FIGS. 8A and 8B schematically illustrate a portion of an eddy current sensor assembly 400 in accordance with a further embodiment of the present invention. The assembly 400 includes a mounting plate 402 coupled to the ferromagnetic bar 18. Two guide plates 406, 406 are coupled to the mounting plate 402, and each extend from a supported end 410 at the mounting plate to a free end 412 to oppose a pipe wall W of a pipe P to be inspected. As shown in FIG. 8A, the guide plates 406, 406 are spaced from one another and cooperate with the mounting plate 402 to form a channel 414 extending along the direction of sensor movement. A sensor body 416 having a supported end 418 and a free end 420 is partially straddled between the guide plates 406, 406 within the channel 414 such that the free end 420 of the sensor body extends beyond the free ends 412, 412 of the guide plates 406, 406 to oppose the pipe wall W. At least one resilient member, such as two coiled springs 421, 421 shown in FIG. 8B, couples the supported end 418 of the sensor body 416 to the mounting plate 402. As best shown in FIG. 8B, the coiled springs 421, 421 extend at an oblique angle α relative to the direction of sensor movement generally from a leading, supported end of the sensor body 416 toward a lagging end of the mounting plate 402. The sensor body 416 at a leading portion of its free end 420 defines a chamfer 422 for engaging a weld bead 36 or other projection or obstruction 37 in the pipe wall W. Each of the plates defines slots 428 aligned with one another in the transverse direction in relation to sensor movement, and each slot extends at an oblique angle α relative to the direction of sensor movement generally from a leading, free end 412 of the guide plate 406 toward a lagging, supported end 410. A mounting pin 430 extends through the sensor body 416 in the transverse direction and its ends 432, 432 are supported in an associated slot 428 of the guide plates 406. When the weld bead 36 or the obstruction 37 exerts a normal force against the chamfer 422 of the sensor body 416, the free end 420 of the sensor body 416 at its leading portion is moved away from the pipe wall W in a direction limited and directed by movement of the pin 430 along the slots 428, 428.

Figure 9:
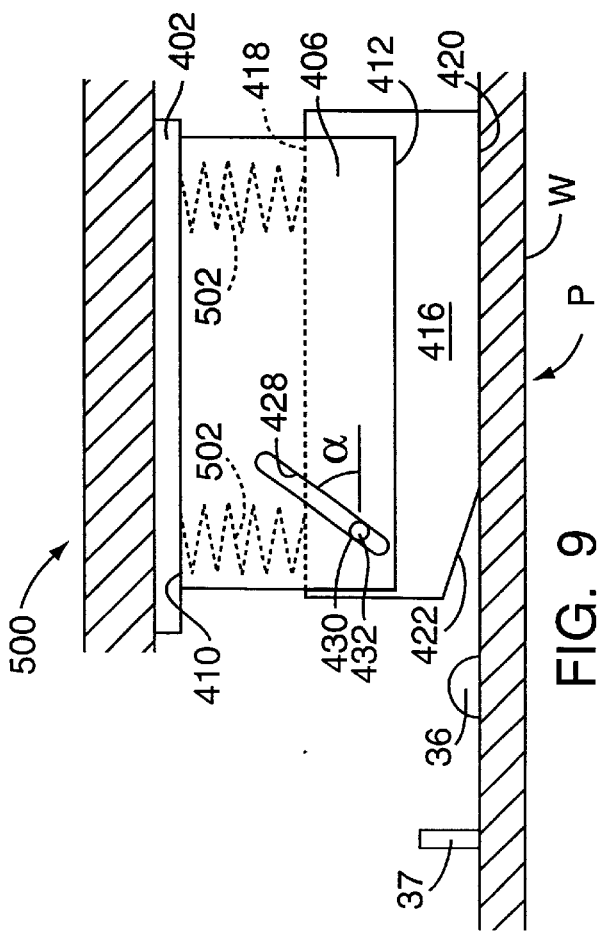
FIG. 9 schematically illustrates an eddy current sensor assembly including guide plates and upright coil springs in accordance with the present invention.

FIG. 9 schematically illustrates a portion of an eddy current sensor assembly 500 which is similar to the eddy current sensor assembly 400 of FIGS. 8A and 8B, except for the resilient means, such as the two coiled springs 502, 502. The coiled springs 502, 502 are longitudinally oriented in a direction perpendicular to sensor movement from the supported end 418 of the sensor body 416 to the mounting plate 402.

Figure 10:
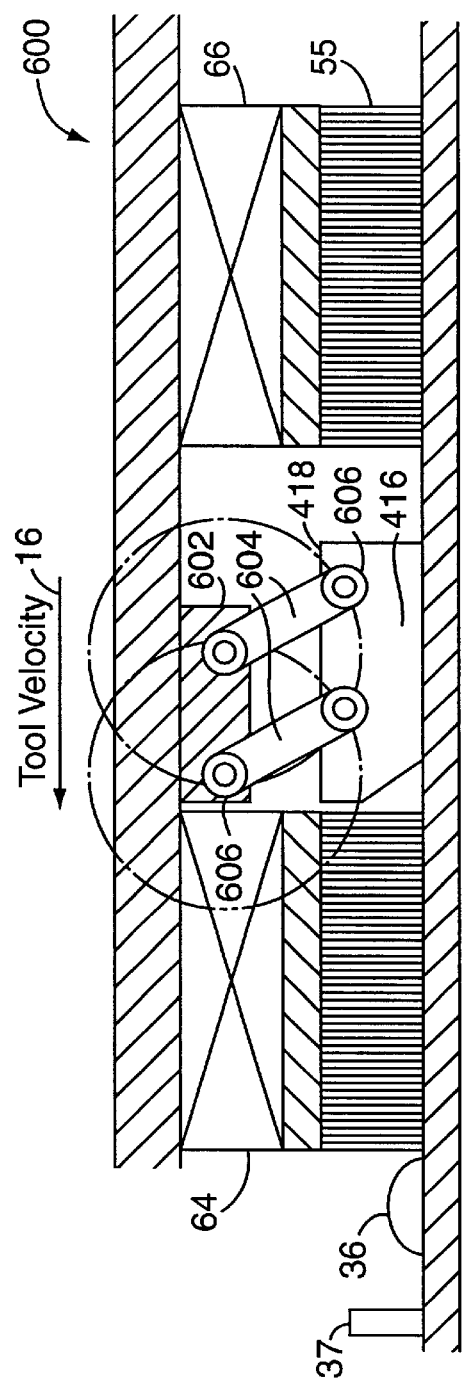
FIG. 10 schematically illustrates an eddy current sensor assembly including link members coupled to a chamfered sensor body in accordance with the present invention.

FIG. 10 schematically illustrates an eddy current sensor assembly 600 in accordance with another embodiment of the present invention. The assembly 600 includes a mounting plate 602 coupled to the ferromagnetic bar 62. The sensor body 416 is radially adjustably coupled to the ferromagnetic bar 62 by means of at least one link member, such as the parallel link members 604, 604 each having first and second longitudinal ends which are respectively pivotally coupled to the supported end 418 of the sensor body 416 and the ferromagnetic bar by means of hinge members 606, 606. The link members 604, 604 are rotationally biased by means of springs (not shown) to urge the sensor body 416 against the pipe wall W.

Figure 11:
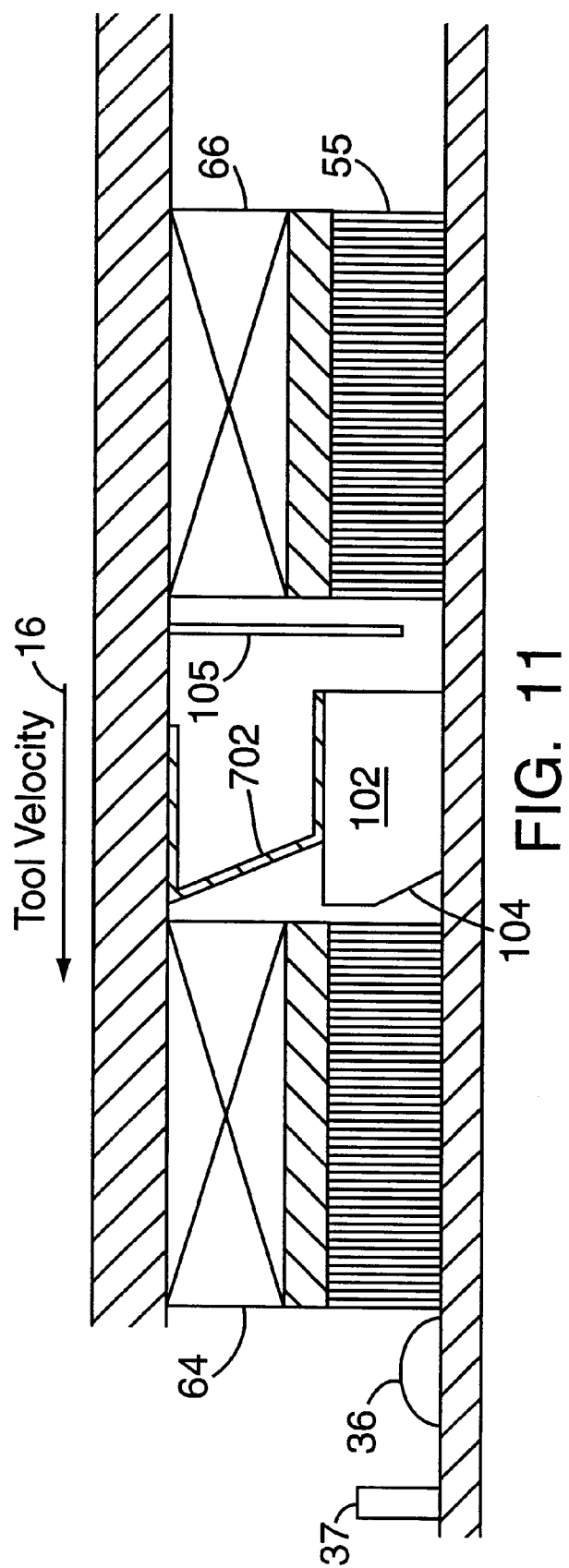
FIG. 11 schematically illustrates an eddy current sensor assembly including a leaf spring and chamfered sensor body in accordance with the present invention.

FIG. 11 schematically illustrates an eddy current sensor assembly 700 in accordance with another embodiment of the present invention. The assembly 700 includes a leaf spring 702 as the resilient member coupled at a first end to the ferromagnetic bar 62 and at a second end to a supported end 118 of a sensor body 102. The shape of the leaf spring 702 facilitates the translation of a normal force exerted by a weld bead 36 or other projection or obstruction 37 against a chamfer 104 of the sensor body 102 into radial movement of the sensor body away from the inspected object and over the weld bead. A stop 105 interposed between the sensor body 102 and the second auxiliary pole 66 prevents the sensor body 102 from contacting and possibly damaging the second auxiliary pole.

While the present invention has been described in several embodiments, it will be understood that numerous modifications and substitutions can be made without departing from the spirit and scope of the invention. Accordingly, the present invention has been described in several preferred embodiments by way of illustration, rather than limitation.

What is claimed is:

1. An eddy current sensor assembly of a magnetic inspection device having first and second primary magnetic poles for inducing a static magnetic flux to at least a near-saturation level through a longitudinal section of an elongated magnetically permeable object extending between the primary poles in order to nondestructively detect structural faults in the elongated magnetically permeable object, the sensor assembly comprising:

magnet means including first and second auxiliary magnetic poles to be interposed between the first and second primary magnetic poles, the first and second auxiliary magnetic poles oppositely polarized relative to each other and spaced from one another for positioning and movement longitudinally relative to an elongated magnetically permeable object to be tested for boosting eddy currents within the magnetically permeable object along a portion of the object between the auxiliary magnetic poles where eddy currents generated by the primary magnetic poles have substantially decayed;

a ferromagnetic member coupling the first and second auxiliary magnetic poles;

compliant pole pieces to be interposed between the first and second auxiliary magnetic poles and the object to be inspected for permitting eddy currents to be boosted in the object even as the auxiliary magnetic poles pass over girth welds or other projections along an opposing surface of the object; and an eddy current sensor disposed between the first and second auxiliary magnetic poles, the sensor including a sensor body and a means coupled to the ferromagnetic member for urging the sensor body against an opposing surface of the magnetically permeable object to be inspected for maintaining contact of the sensor with an opposing surface of the object in order to detect changes in eddy currents due to structural faults even as the sensor moves over girth welds or other projections.

2. An eddy current sensor assembly as defined in claim 1, wherein the urging means is a resilient member.

3. An eddy current sensor assembly as defined in claim 2, wherein the resilient member is a coil spring.

4. An eddy current sensor assembly as defined in claim 2, wherein the resilient member is a leaf spring.

5. An eddy current sensor assembly as defined in claim 2, wherein the resilient member is an elastic block.

6. An eddy current sensor assembly as defined in claim 1, wherein the urging means includes:

two guide plates coupled at edge surfaces to the ferromagnetic member and spaced from one another in a direction transverse to sensor movement, the sensor body being straddled between the guide plates, the guide plates and ferromagnetic member cooperating to form a channel for receiving the sensor body, the guide plates each defining a slot; and an elongated guide member fixedly extending through the sensor body and supported at each end by an associated slot of the guide plates for directing the movement of the sensor body along a path defined by the slots in a direction generally away from an opposing surface of the object to be inspected as the sensor body contacts and moves over a girth weld or other projection in the object.

7. An eddy current sensor assembly as defined in claim 1, wherein the sensor body defines a chamfer at a leading edge of the sensor body relative to sensor movement for facilitating the movement of the sensor body over a gird weld or other projection in the object to be inspected.

8. An eddy current sensor assembly as defined in claim 1, wherein the compliant pole pieces are brushes.

9. An eddy current sensor assembly as defined in claim 8, wherein the brushes are steel brushes.

10. An eddy current sensor assembly as defined in claim 1, wherein the magnet means is a permanent magnet.

11. An eddy current sensor assembly as defined in claim 1, further including an additional eddy current sensor disposed on a leading side of the magnet means.

12. An eddy current sensor assembly as defined in claim 1, further including a stop member interposed between the eddy current sensor and at least one of the auxiliary magnetic poles for preventing the sensor from contacting the auxiliary magnetic poles.

13. An eddy current sensor assembly as defined in claim 1, further including a digital processor responsive to sensor signals for determining the location and magnitude of a structural fault within the moving portion of the object.

14. A magnetic inspection device for nondestructively detecting structural faults in magnetically permeable elongated objects, comprising:

first and second primary magnetic poles oppositely polarized relative to each other and spaced from one another for positioning and movement longitudinally relative to an elongated magnetically permeable object to be tested, the first primary magnetic pole being positioned upstream of the second primary magnetic pole relative to magnetic pole movement;

a ferromagnetic member magnetically coupling the first and second primary magnetic poles;

first and second auxiliary magnetic poles magnetically coupled to the ferromagnetic member and interposed between the first and second primary magnetic poles, the first auxiliary magnetic pole being positioned upstream of the second primary magnetic pole, the first and second auxiliary magnetic poles respectively having the same poling as the first and second primary magnetic poles, the primary magnetic poles inducing eddy currents and a static magnetic flux through a longitudinal section of an object extending between the primary magnetic poles to at least a near-saturation level, the auxiliary magnetic poles boosting the magnitude of the induced static magnetic flux in a portion of the object adjacent to the auxiliary magnetic poles, the primary magnetic poles inducing eddy currents and an associated opposing magnetic flux in a moving portion of the object adjacent to the first primary magnetic pole, and the auxiliary magnetic poles boosting circumaxial eddy currents and inducing an associated opposing magnetic flux in a moving portion of the object adjacent to the first auxiliary magnetic pole where eddy currents induced by the primary magnetic poles have substantially decayed;

compliant pole pieces coupled to the primary and auxiliary magnetic poles to be interposed between the poles and the object to be inspected for permitting eddy currents to be boosted in the object even as the auxiliary magnetic poles pass over girth welds or other projections along an opposing surface of the object; and an eddy current sensor disposed between the first and second auxiliary magnetic poles, the sensor including a sensor body and a means coupled to the ferromagnetic member for urging the sensor body against an opposing surface of the magnetically permeable object to be inspected for maintaining contact of the sensor with an opposing surface of the object in order to detect changes in eddy currents due to structural faults even as the sensor moves over girth welds or other projections.

15. A magnetic inspection device as defined in claim 14, wherein the urging means is a resilient member.

16. A magnetic inspection device as defined in claim 14, wherein the urging means includes:

two guide plates coupled at edge surfaces to the ferromagnetic member and spaced from one another in a direction transverse to sensor movement, the sensor body being straddled between the guide plates, the guide plates and ferromagnetic member cooperating to form a channel for receiving the sensor body, the guide plates each defining a slot; and an elongated guide member fixedly extending through the sensor body and supported at each end by an associated slot of the guide plates for directing the movement of the sensor body along a path defined by the slots in a direction generally away from an opposing surface of the object to be inspected as the sensor body contacts and moves over a girth weld or other projection in the object.

17. A magnetic inspection device as defined in claim 14, wherein the sensor body defines a chamfer at a leading edge of the sensor body relative to sensor movement for facilitating the movement of the sensor body over a gird weld or other projection in the object to be inspected.

18. A magnetic inspection device as defined in claim 14, wherein the compliant pole pieces are brushes.

19. A magnetic inspection device as defined in claim 14, further including an additional eddy current sensor disposed on a leading side of the first auxiliary magnetic pole.

20. A magnetic inspection device as defined in claim 14, further including a digital processor responsive to sensor signals for determining the location and magnitude of a structural fault within the moving portion of the object.

* * * * *